United States Patent [19]

Cornut et al.

[11] Patent Number: 4,623,519
[45] Date of Patent: Nov. 18, 1986

[54] CELL FOR ANALYSIS DEVICE, TO COLLECT A FRACTION OF A LIQUID SAMPLE FOR REACTION AND ANALYSIS

[75] Inventors: Bruno Cornut, Montardon; Claude Chambu, Billere; Jean-Louis Seris, Jurancon, all of France

[73] Assignee: Societe Nationale Elf Aquitaine, Courbevoie, France

[21] Appl. No.: 626,749

[22] Filed: Jul. 2, 1984

[30] Foreign Application Priority Data

Jul. 27, 1983 [FR] France ................ 83 12425

[51] Int. Cl.$^4$ .................. G01N 21/07; G01N 21/75; G01N 31/00
[52] U.S. Cl. ............................ 422/72; 356/246; 436/45
[58] Field of Search ............... 422/72, 102, 100, 56, 422/58; 436/45; 356/246, 244, 440

[56] References Cited

U.S. PATENT DOCUMENTS

| | | | |
|---|---|---|---|
| 3,715,192 | 2/1973 | Wenz et al. | 422/56 |
| 4,154,793 | 5/1979 | Guigan | 422/72 X |
| 4,233,029 | 11/1980 | Columbus | 422/55 X |
| 4,314,970 | 2/1982 | Stein et al. | 422/72 |
| 4,373,812 | 2/1983 | Stein et al. | 422/72 X |

FOREIGN PATENT DOCUMENTS 2506015 11/1982 France .

Primary Examiner—Arnold Turk
Attorney, Agent, or Firm—Burgess, Ryan & Wayne

[57] ABSTRACT

The present invention relates to a fractionating and observation cel of a liquid analysis device comprising a rotor, a central distribution cup or container for said liquid, and an assembly of cells on the periphery of the rotor, wherein the cells and the duct are formed by welding of two plastic pieces comprising said rotor, the liquid feed and gas evacuation duct is provided by the space existing between the two plastic pieces welded to each other by two welding seams along the edges of each duct, the opposite faces of the said pieces that constitute the duct with the said seams being left rough from molding.

2 Claims, 6 Drawing Figures

CELL FOR ANALYSIS DEVICE, TO COLLECT A FRACTION OF A LIQUID SAMPLE FOR REACTION AND ANALYSIS

BACKGROUND OF THE INVENTION

FIELD OF THE INVENTION

The present invention relates to a cell for fractionating and observing a liquid in a device for analysing this liquid comprising a rotor, a central distribution container for said liquid, and an assembly of such fractionating cells on the periphery of the rotor, each connected to the cup by a liquid feed and gas evacuating duct parallel to the feed duct.

French Patent No. 81019496 filed on May 13, 1981 in the name of the Societe Nationale Elf Aquitaine concerns such a cell. In fact, the cell according to this French patent which discloses a liquid analysis device, is intended to collect a liquid sample fraction to be analyzed in identical cells arranged on the periphery of the rotor. The rotation of this rotor, and the effect of the centrifugal force resulting therefrom, is used to effect the distribution of the liquid fraction delivered to the various identical analysis cells, from a central distribution cup or container.

Each sampled fraction is contacted with a reactive agent comprising an indicator, and is then examined through the cell walls, by means of a suitable device.

The various embodiments described in this French Patent No. 8109496 relate to preventing the formation of air and gas bubbles in the cell; or more precisely, to facilitating the evacuation of such bubbles during the centrifugation by permitting a complete filling of the said cell.

Furthermore, the embodiments described in this French Patent No. 8109496 concern, more especially, ducts for the liquid feed and gas evacuation of the cell, these ducts being able, possibly, to coincide along a part of their length. In particular, it is foreseen to realize cells and ducts through molding plastic pieces welded to one another, with ribs being provided on the internal face of one and/or other of these sheets permitting the said ducts. It is, of course, advantageous to reduce, as much as practically possible, the volume of the ducts that constitutes harmful empty spaces.

The ojects of the present invention is to provide a cell and ducts from molded plastic pieces, and presenting extremely reduced empty spaces, this cell allowing, furthermore, an evacuation as complete as possible of the gases as well as a filling as complete as possible of the cell system, by the liquid to be analyzed.

The fraction collecting and analysing cell device according to the invention comprises a rotor, a central distribution cup of the said liquid, an assembly of such fraction and analysing cells on the periphery of the rotor, each connected to the cup by a liquid feed and gas evacuation cup coinciding in a single channel, cell and duct being formed through molding of plastic pieces, in a manner known per se, and the liquid feed and gas evacuation duct being formed by the space existing between the two plastic pieces welded to each another by two welding seams along the edge of the said duct the opposite faces of the said pieces that constitute the duct with the said welding lines being left in the rough state from molding.

In a surprising way, the irregularities and asperities of the rough molding faces of the two faces forming the liquid feed and gas evacuation duct, are sufficient to allow between these pieces the free passage, not only of the gases, but also the liquid.

A complete filling of the cell is thus obtained, through a bubble-free liquid.

Of course, the realization of this cell is particularly economic and simple.

BRIEF DESCRIPTION OF THE DRAWINGS

The advantages and characteristics of the present invention will, furthermore, appear more evident from the following description, given simply by way of example, with reference to the annexed drawings in which:

FIG. 1 represents the central distribution cup 1 of the liquid to be fractionated, which forms part of the rotor (not represented) of the prior art device which is connected to a conventional manner, by a radial capillary duct 2 to the analysis cell 3. Preferably, this cell 3 constitutes a volume that is calibrated with precision. The device comprises in fact a plurality of cells distributed about the cup 1, on the periphery of the rotor.

The liquid feed capillary duct 2 coincides with the evacuation passage of the gas.

The different embodiments represented allow good bubble-free filling of the cell and thus facilitate observation of the sample.

Figure 1:
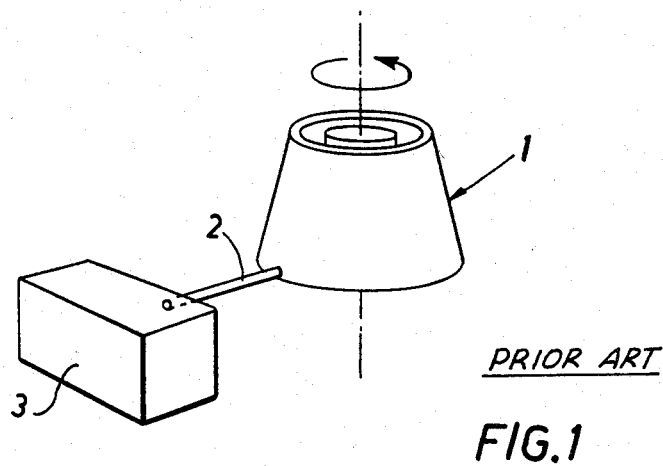
FIG. 1 is a partial view of a cell described in French Patent No. 81019496 with it connection duct to the central cup of the rotor.
Figure 2:
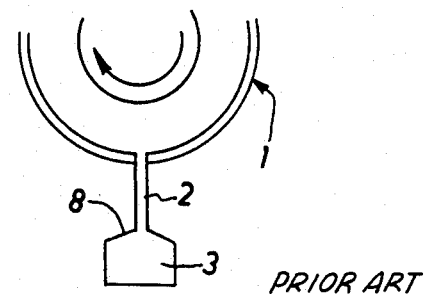
FIG. 2 represents another embodiment according to the invention, showing a particular form of the distribution cup seen from below.

The invention foresees, however, a disposition allowing to further improve the filling, especially by a localization of the remaining bubble in a site of the cell situated outside the optical beam, for example, by providing curviture of the wall of the cup, at its connection with the gas evacuation passage (FIG. 2).

Figure 3:
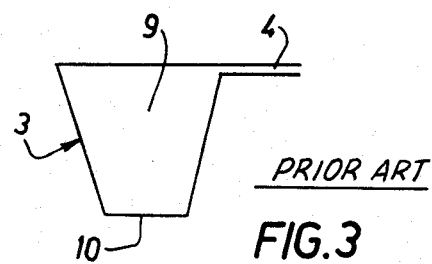
FIG. 3 represents one embodiment of the tronconic cell.

It is also possible to realize conical cells (FIG. 3) the axis of which is parallel to the axis of the rotor, divergent towards the top, this form facilitating the evacuation of the gases. Of course, in this case, the optical sighting will be made according to an axis parallel to the axis of the cone; in other words, cover 9 and bottom 10 of the cell in the form of a truncated cone will thus be parallel and perpendicular to this axis of the cone.

DESCRIPTION OF THE PREFERRED EMBODIMENTS

Figure 4:
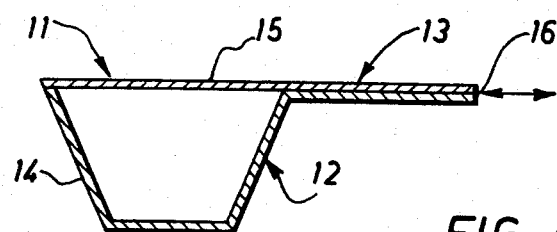
FIG. 4 is a schematic diagram in transversal section of one cell according to the present invention.

In the design application of FIG. 4, the cell 11 according to the invention from two molded plastic pieces 12 and 13 welded to each other, comprises a cup 14, provided in the piece 12 and closed by a cover 15, provided by the pieces 13, and a duct 16, issuing at the said cup, realized between the two pieces 12 and 13 by two longitudinal welding seams 17 and 18 (FIG. 5) edging the said duct 16.

The faces in contact of the pieces 12 and 13, which constitute with weldings 17 and 18 the duct 16 are left in the rough state from molding and, in a surprising way, the surfaces asperities and irregularities of the said pieces are sufficient to provide a passage which is both efficient for the liquid feed and the gas evacuation.

Figure 5:
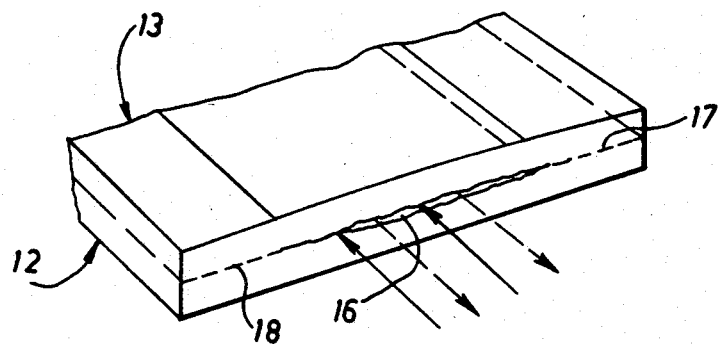
FIG. 5 is a view in section on a larger scale, of the part of the cell represented in FIG. 4, that forms the liquid feed and gas evacuation duct.

For enhanced simplicity, these asperities and irregularities have been very strongly accentuated in their representation in FIG. 5. Indeed, the surfaces such as they leave rough from molding can be used.

Figure 6:
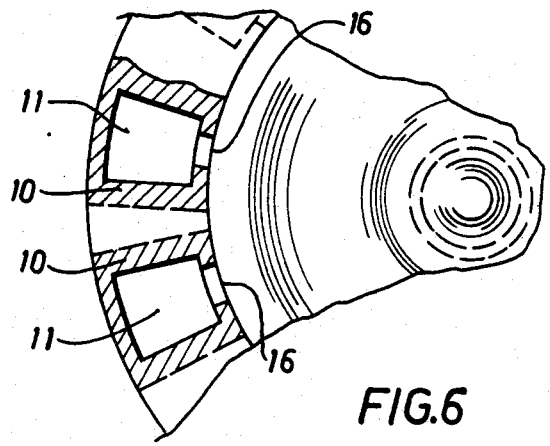
FIG. 6 is a partial view from below of an analysis device comprising a plurality of cells according to the present invention.

FIG. 6 represents part of the analysis device comprised of a plurality of cells 11. The hatched zones 10 surrounding these cells correspond to the weldings that form the edge the said cells and, at the same time, define the duct 16.

What is claimed is:

1. A rotor for a fractionating and observation cell for a liquid analysis device comprising: a central distribution container for a liquid, a plurality of fractionating cells on the periphery of the rotor, each cell being connected to the container by a liquid feed and gas evacuation duct wherein the cells and duct are formed of molded plastic pieces, each liquid feed and gas evacuation duct comprises a space between two substantially planar plastic pieces which are welded to each other by two welding seams, the welding seams forming the edges of said duct, and wherein the portions of said pieces that comprise the duct are left rough from molding.

2. In a rotor for a liquid analysis device comprising a central liquid distribution container in the form of a body of revolution and a plurality of sampling and viewing cells connected to said central container around the periphery thereof, each cell in fluid communication with said container through duct means for feeding liquid from said container to the associated cell and wherein each cell has gas evacuating means for evacuating gas therefrom, the improvement wherein the duct means and gas evacuating means for each cell comprise a non-bonded area providing a passageway for said liquid and gas, the non-bonded areas being formed between first and second plastic sheets which extend from said cells to said central container; and wherein for each liquid and gas passageway said plastic sheets are bonded to each other in two bonding areas delimiting between said bonding areas said non-bonded area which, due to the normal surface roughness of said plastic sheets as molded, permits passage of both said liquid and gas.

* * * * *

UNITED STATES PATENT AND TRADEMARK OFFICE
CERTIFICATE OF CORRECTION

PATENT NO. : 4,623,519

DATED : November 18, 1986

INVENTOR(S) : Bruno Cornut, et al

It is certified that error appears in the above-identified patent and that said Letters Patent is hereby corrected as shown below:

On the title page assignee should read

-- (73) Assignee: Inovelf, Societe Anonyme, Paris,

France --.

Signed and Sealed this

Eighteenth Day of August, 1987

*Attest:*

DONALD J. QUIGG

*Attesting Officer*      *Commissioner of Patents and Trademarks*